United States Patent

Seidel et al.

[11] Patent Number: 6,137,584
[45] Date of Patent: Oct. 24, 2000

[54] METHOD AND DEVICE FOR DETERMINING PREDETERMINED PROPERTIES OF TARGET PARTICLES OF A SAMPLE MEDIUM

[75] Inventors: Claus Seidel; Leif Brand, both of Göttingen; Rolf Gunther, Hamburg, all of Germany

[73] Assignees: Max-Planck-Gesellschaft Zur, Munich; Evotec BioSystems Aktiengesellschaft, Hamburg, both of Germany

[21] Appl. No.: 09/308,452

[22] PCT Filed: Nov. 26, 1997

[86] PCT No.: PCT/EP97/06601

§ 371 Date: Aug. 11, 1999

§ 102(e) Date: Aug. 11, 1999

[87] PCT Pub. No.: WO98/23941

PCT Pub. Date: Jun. 4, 1998

[30] Foreign Application Priority Data

Nov. 27, 1996 [DE] Germany ............................ 196 49 048
Jan. 28, 1997 [DE] Germany ............................ 197 02 914

[51] Int. Cl.[7] .................................................. G01N 21/55
[52] U.S. Cl. ........................... 356/445; 446/448; 446/213
[58] Field of Search ..................................... 356/445, 446, 356/448, 213

[56] References Cited

U.S. PATENT DOCUMENTS

5,434,667  7/1995  Hutchins et al. ........................ 356/338

Primary Examiner—Frank G. Font
Assistant Examiner—Reginald A. Ratliff
Attorney, Agent, or Firm—Fay, Sharpe, Fagan, Minnich & McKee, LLP

[57] ABSTRACT

A method and device are disclosed for expanding the field of application of florescent correlation spectroscopy. The device has a confocal optical structure, a pulsed laser for excitation and components for detection and evaluation of measuring signals for time-correlated single photon counting. The data is registered in such a way that for each detected photon, detection time is recorded in microseconds while fluorescence delay time is recorded in nanoseconds. The information on each detected photon is used to assign parameters determined by time-correlated single photon counting to each detected photon and to create correlation functions from the determined parameters arising therefrom. Correlation functions of parameters or selective correlation functions, e.g. for fluorescence burning life, are thus obtained. The method and the device can also be used to detect individual molecules and to calculate correlation functions only for those signal segments which are assigned to the individually existing particles, thereby improving the signal-to-noise ratio in extremely diluted solutions.

24 Claims, 7 Drawing Sheets

METHOD AND DEVICE FOR DETERMINING PREDETERMINED PROPERTIES OF TARGET PARTICLES OF A SAMPLE MEDIUM

The invention relates to a method according to the preamble of claim 1 and a method according to the preamble of claim 15 and to an arrangement according to the preamble of claim 18.

Time-correlated single-photon counting is a versatile spectroscopic technique whereby a number of parameters of particles under investigation can be determined. These properties include the fluorescence life or the various fluorescence lives of multi-exponential decays, rotation diffusion constants, kinetic transition rates, among others. In addition, the high time resolution associated with time-correlated single-photon counting, in conjunction with pulsed excitation, is an effective means of separating non-delayed scattered excitation light from delayed fluorescent light. By this means, the desired signal (fluorescence) can be separated from undesired noise (non-delayed scattered light) and the signal-to-noise ratio in many applications can be increased.

Other properties, particularly the diffusion constant of target particles, can be obtained by the method of fluorescence correlation spectroscopy (FCS). A knowledge of the diffusion constant yields a variety of information about the size of the target particles or the bonding thereof to other large molecules.

In conventional FCS measuring methods (compare WO 94/16313), however, there is no possibility of discriminating between non-delayed scattered excitation light and delayed fluorescence light, so that the signal-to-noise ratio is too low.

Both techniques, i.e. time-correlated single-photon counting and fluorescence correlation spectroscopy, are suitable for highly sensitive measurements on very dilute solutions of fluorescent particles, preferably in the sub-nanomolar range. These techniques can even detect individual molecules in sample media (compare C. Zander et al., Applied Physics B, Volume 63, pages 516–523, 1996). Hitherto, however, it has not been possible to determine the autocorrelation function of signals from individual particles.

A method and an arrangement of the kind mentioned in the preamble were described by Richard A Keller et al. in Applied Spectroscopy, Volume 50, No. 7, 1996, on pages 12A to 32A. The possibilities of data analysis by the arrangement described are limited to isolated use of the evaluation possibilities either of time-correlated single photon counting or of FCS. The advantages of both techniques are not used in combination. Furthermore the evaluating device in the arrangement known from the citation uses a complicated and expensive CAMAC frame and needs a multi-channel scaler (MCS).

The object of the invention is to extend the possible uses of fluorescence correlation spectroscopy.

According to the invention this problem is solved by a method having the features of claim 1, a method having the features of claim 15 and an arrangement having the features of claim 18.

In the first embodiment of the method according to the invention for determining predetermined properties of target particles in a sample medium, the sample medium is initially irradiated with periodically modulated light having a predetermined period. Preferably the sample medium is irradiated with a regular sequence of uniformly spaced light pulses. The distance between two light pulses (the period) is e.g. 12 ns. Next, light in the form of individual photons scattered in the sample medium is detected by a detection device. On the one hand, the time interval between the time of detection of each photon and a reference time within the associated period of the irradiating light is determined and defined as the delay time. On the other hand the time of detection of each photon is determined. This is usually done by means of two different measuring arrangements adapted to the particular measurement requirements. The delay time, which is in the nanosecond range, requires an analog measuring arrangement for measuring extremely short-duration processes. The times of detection on the other hand are usually determined by a digital measuring arrangement, adapted to measure the corresponding times in the microsecond range.

The method according to the invention is characterised in that firstly at least one parameter of the scattered light is determined, using the delay times for a respective number of successively detected photons.

The number of successively detected photons can e.g. be fixed and predetermined or adapted to the presence of target particles in the sample space. A first parameter value is determined for a number of successively detected photons. Next a second parameter value is determined from the delay times of a further number of successively detected photons. The second number of successively detected photons may follow the previous number of detected photons or alternatively the second number of photons may include (overlap) a part of the first number of photons. In the first case the successively detected photons are divided into successive groups, in each of which a parameter value is determined. In the second case, substantially, a selected-time window slides over the successively detected photons, and the delay times of the photons within the time window are used to form the parameter value.

In order to determine a parameter value from the delay times, additional information is generally used, obtained from a pre-evaluation of certain properties of the particles. These properties are e.g. in the form of spectroscopic data, such as previously known fluorescence lives. The delay times for a predetermined number of successively detected photons are then evaluated, using the recorded spectroscopic data. For example, the proportional amplitude of non-delayed scattered light and delayed fluorescent light can be quantitatively analysed.

The parameters and the associated times of detection of the successively detected photons are then used to obtain pairs of parameter and time values, and a number of pairs of parameter and time values is used to determine at least one parameter-time function. A correlation function of the at least one parameter-time function is then calculated. Correlation of the resulting parameter-time function yields extended, novel information about properties of the particles.

Application according to the invention of correlation technology to the parameter values obtained by time-correlated single-photon counting is a means of determining novel properties of the target particles and extends the possibilities of the known techniques. For example, the autocorrelation function of the isolated amplitude component of the component of the scattered light attributable to fluorescence can be calculated. This effectively suppresses background signals. The calculated correlation functions can be used e.g. to determine the diffusion constant of the target particle. As compared with conventional FCS, the method according to the invention appreciably improves the signal-to-noise ratio. The method according to the invention enables measurements of this kind to be made for the first time in ultra-dilute solutions.

In an advantageous further feature of the method according to the invention, the light scattered in the sample medium is detected by more than one detector. At least one parameter-time function is then calculated separately for the photons detected by each detector.

Preferably, the correlation function is then calculated in the form of a cross-correlation function using the parameter-time functions from various detectors. This enables the bonding reactions between particles to be exactly observed, e.g. by using different spectral filters in the individual detection branches.

In an alternative embodiment of the method for determining predetermined properties of target particles in a sample medium, the sample medium is first irradiated with light, after which light in the form of individual photons scattered in the sample medium is detected by a detection device, and the time of detection of each scattered photon is detected. The density distribution of the target particles is chosen so that on average less than one target particle is present in an observed volume element of the sample medium (sample space). The measured times of detection are evaluated in order to find the time interval during which a target particle was individually present in the sample space. This is done e.g. by measuring the time intervals between successive times of detection, entry of a target particle into the sample space being recognised e.g. when a predetermined number of time intervals falls below a maximum interval. Alternatively, for example, the number of measured detection times in a predetermined time interval can be evaluated, in which case the presence of a target particle in the sample space is assumed if the number of times of detection measured per unit time falls below a minimum value.

The method according to the invention is characterised in that a correlation function is calculated exclusively by means of those times of detection which occur within the thus-determined time interval (during which target particles are present in the sample space) and in that the predetermined properties of the target particles are determined by means of the said correlation function.

In the method according to the invention, in contrast to the prior art, the measured times of detection are selected before a detection function calculated by means of the times of detection is subjected to correlation. The detection function can e.g. be a scanning function which assumes the value zero if no photon was detected during the scanning-time interval, or the value one if a detection occurred in the scanning interval. If the chosen time interval is larger, the detection function can also represent the number of times of detection measured in the respective constant time intervals.

In the arrangement according to the invention, in the case of all the detected photons, the time intervals between the respective times of detection of the photons and a reference time for the respective period of the irradiating light, i.e. the delay times, are determined and also the time intervals between successive times of detection of photons are determined by using the counter arrangement. The two times are associated in pairs and stored.

According to the invention the time interval between successive times of detection of photons is determined by an alternating counter arrangement which contains at least a first and a second counter. It is controlled by electric pulses from the detection device and is so connected that the counters count alternately, i.e. if a photon has been detected, the resulting pulse starts the first counter. If a second photon is detected, the associated electric pulse from the detection device stops the first counter and starts the second counter. While the second counter is counting, the count of the first counter can be transmitted to the downstream computer unit. When a third photon arrives, the second counter is stopped and the first counter is restarted. In the next moment the count of the second counter can be read out and transmitted to the downstream computer unit while the first counter starts counting again.

One advantage of the arrangement according to the invention is that it can be constructed from very simple means, e.g. counters and known circuit elements.

Another advantage is that the arrangement operates without idle time or loss. When a counter is being reset, the other count is ready for counting.

Finally a further advantage of the arrangement according to the invention is that the time resolution attainable thereby for determining the times of detection of photons is very high and can be flexibly predetermined.

The invention enables single or a few molecules to be spectroscopically investigated with reasonably priced apparatus and with high accuracy and a variety of analytical possibilities. By means of the invention, the light scattered by the target particles is effectively separated from interfering background signals and consequently the desired properties of the target particles can be measured with previously unattainable accuracy.

Advantageous further features of the invention are disclosed in the sub-claims.

The invention will now be explained in further detail with reference to exemplified embodiments shown diagrammatically in the drawings. Like reference numbers in the individual drawings denote like elements. More particularly

The method according to the invention and the arrangement according to the invention have multiple uses.

The property of a target particle to be determined can e.g. be its capacity to bond to another molecule or the value of its diffusion constant in a given sample medium. "Properties" also includes states or changes of state of the target particles. Possible states of the target particles can accordingly be e.g. the bonded state or the free state. Changes of state can be transitions between "bonded" and "free" or transitions between various electronic states of the target particle. In the simplest case the change can be the transition between the first excited singlet and the fundamental electronic state, i.e. fluorescence. The reciprocal of the associated speed constants is the fluorescence life.

Target particles are particles to be spectroscopically measured or detected. They are in or on the sample media. Target particles can be molecules or molecular aggregates or complexes. The technique can also be applied to atoms, microbiological objects such as viruses, organelles or cells and membranes, or other small objects such as latex spherules.

The sample medium is usually a liquid medium, particularly a solvent for the target particles. The sample medium may typically be an organic solvent, water or suitable buffer solutions for biological investigations, or blood or fungal or bacterial culture media. The sample medium can be liquid, solid or gaseous, homogenous or heterogeneous, i.e. made up of different phases. It can for example consist of two phases, e.g. a liquid or gas above a solid surface.

The sample space is a volume element of the sample medium observed by the arrangement according to the preamble.

The light irradiating the target particles of sample medium in the sample space can be visible light or ultraviolet or infrared light. In the most general case the light is electromagnetic radiation which can be scattered by the target particles.

The light can be modulated as desired, provided it has a fixed period. More particularly it can be pulsed or sinusoidally modulated with a suitable offset.

The light can be scattered in numerous ways. More particularly the light can be scattered elastically or inelastically, i.e. retaining or changing its wavelength. Also it may be non-delayed or delayed. Delayed elastic scattering includes luminescence, particularly fluorescence, with typical delay times of a few nanoseconds.

The detection device in the arrangements according to the preamble usually comprises a suitable optical structure, one or more detectors and a downstream electronic unit for processing the detection signals and usually including analog-digital conversion.

The evaluating device in the arrangement according to the preamble usually comprises an interface for receiving the data from the detection device and a calculating unit, frequently a computer.

The times of detection of the photons can be obtained by absolute determination since the beginning of the measurement or by determining the time interval between the times of detection of successively detected photons. The two cases can be converted into one another by subtraction or by adding the time intervals.

The parameters for determining can be any parameters which can be determined by time-correlated single-photon counting. Examples of such parameters are fluorescence lives, if required also the various fluorescence lives of multi-exponential decays, rotation diffusion constants, kinetic transition rates, photon numbers or total amplitudes or amplitude components of individual components of the scattered light, or any form of statistical measures of distance between the measured and the desired signal, e.g. the least-square distance or an information measure as described in M. Köllner, Applied Optics, Volume 32 (6) (1993), pages 806–820.

Correlation functions can be auto- or cross-correlation functions of given parameters, e.g. the autocorrelation functions of given amplitude components or be cross-correlation functions of given fluorescence lives.

Some exemplified embodiments of the arrangements according to the invention will now be discussed at further length, showing in detail how the properties of target particles can be obtained from data acquired by the arrangements according to the invention.

First we shall consider the optical structure. Usually it is in the form of a confocal or near-field optical structure. In the case of a near-field optical structure, which has the maximum local resolution, the light from the light source for irradiating or stimulating the target particles is sent through an aperture on to the sample medium. The aperture is at a distance of only about 100 nm from the sample space. Also the diameter of the aperture is smaller than the wavelength of the exciting light. The result is extremely local limitation of the intensity distribution of the exciting light around the aperture. A near-field optical structure of this kind is particularly suitable for controlled approach to individual target particles resting on a surface.

A confocal structure having maximum sensitivity is adapted to irradiate a small volume element in a sample medium, e.g. the sample space, and to observe it. Typically to this end the target particles are allowed to diffuse into and out of the volume under observation. Alternatively, the target particles can be conveyed or moved into the sample space in a flow system or otherwise.

Figure 1:
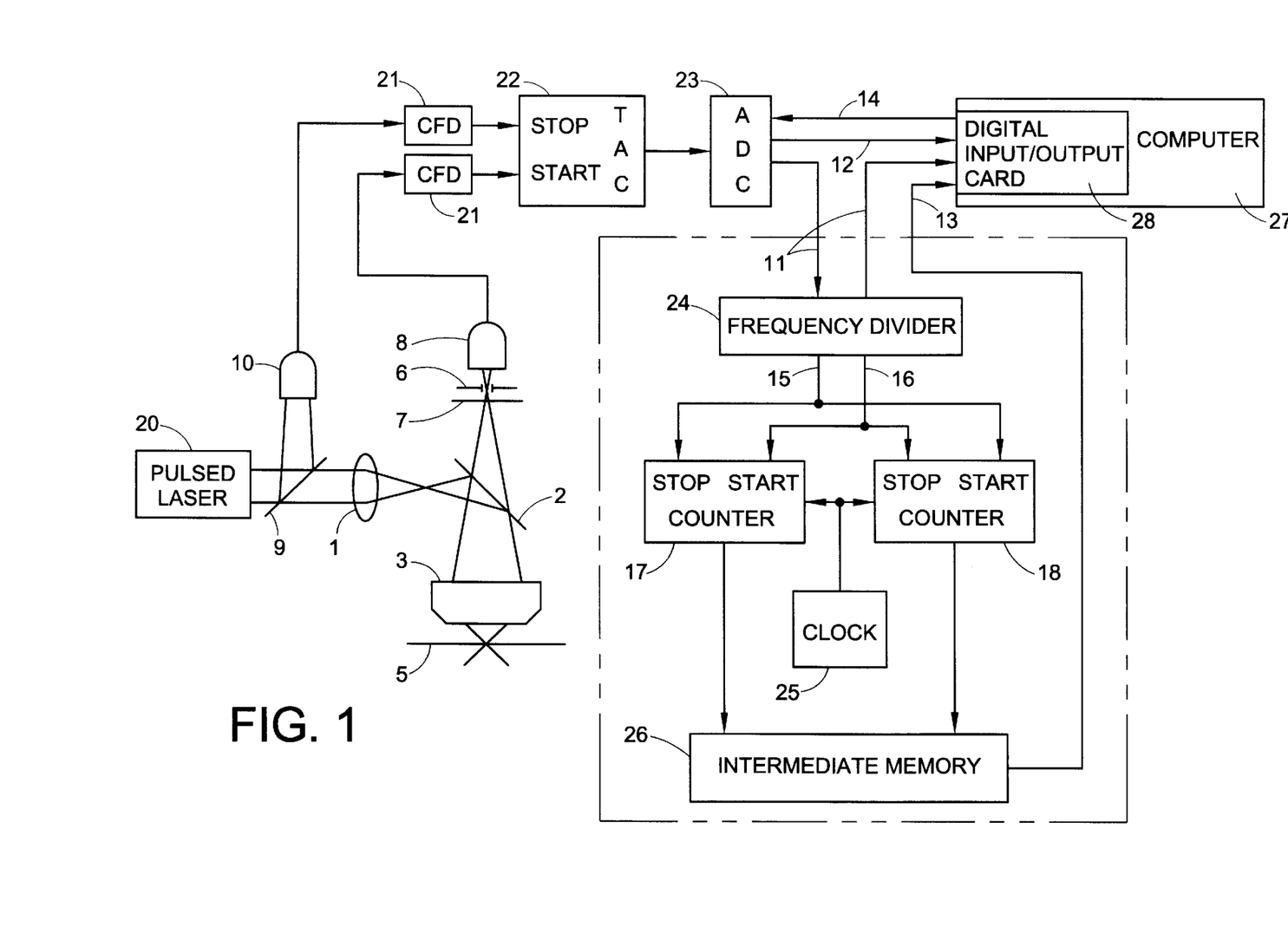
FIG. 1 is a block diagram of a first exemplified embodiment of the invention.

Reference will now be made to FIG. 1. The light source shown in FIG. 1 is a pulsed laser 20. Typically use is made of a mode-coupled laser or a pulsed diode laser which emits pulses having a length between about 100 fs (femtoseconds) and about 500 ps (picoseconds) depending on the nature of the laser, at intervals of about 10 to 30 ns (nanoseconds). Light sources with longer pulses or longer pulse intervals have been found disadvantageous.

According to the invention a pulsed light source can be replaced by a periodically modulated light source. The measured signals are then analysed by evaluating both the change in amplitude and the change in phase of the scattered light relative to the exciting light. A more detailed description of this method of measurement can be found in J. R. Lakowicz: "Principles of fluorescence spectroscopy", Plenum Press, New York, 1983.

In the case of the confocal structure shown in FIG. 1, the laser light is focused by a lens 1 on to a point. In the subsequent path of the beam, the laser light is deflected by a dichroic mirror 2 on to a microscope objective. The dichroic deflecting mirror is constructed so that it reflects the laser light but transmits the longer-wave scattered or fluorescence light from the target particles. Using the deflecting mirror 2 and the microscope objective, the focal point of the laser is imaged at a point inside the sample medium. The sample medium can e.g. be on a sample-holder 5 in the form of a microscope slide. The point illuminated by the laser 20 inside the sample medium is imaged on a pinhole 6 or a diaphragm, using the microscope objective. A spectral filter 7 for separating desired from undesired scattered-light components by colour is disposed in front of the pinhole. Directly behind the pinhole is a detector 8 which is sensitive enough to detect individual photons. This purpose can be served by photomultipliers, microchannel-plate photomultipliers, avalanche photodiodes, or CCDs with or without upstream image amplifiers. A more detailed description of a confocal structure can be found in: G. Kalusche et al., Experimental Technique of Physics, Vol. 41 (2) (1995) pages 265–273, or in M. Eigen, R. Rigler, Proceedings of the National Academy of Sciences of the U.S.A., Vol. 91 (1994), pages 5740–5747.

In addition to the signal from the photodetector 8, a synchronisation signal from the laser 20 is needed. This can either be a direct electric signal output by the electronic unit controlling the laser, or can be derived from the laser light itself. To this end, a part of the laser light is deflected on to a detector 10, using a beam splitter 9 disposed in the path of the beam from the laser 20. The detector 10 can e.g. be a photodiode.

In order to determine the time of detection of a photon scattered in the sample medium, it is necessary to determine the time interval between the time of excitation or of the laser pulse and the time of emission of the photon. If the scattered light is fluorescence, the time interval is also called the "fluorescence delay time". It can be determined by determining the time interval between the trigger pulse emitted by the detector 10 and the time of detection of a photon in detector 8.

Owing to the electrical and optical structure, there is usually a constant delay between a trigger pulse from the detector 10 and the time when a non-delayed scattered photon is detected by the detector 8. This delay, which is always constant for all other detected photons, can be compensated by suitable calibration and suitable delay elements.

To remove any possible jitter, the electric pulses from the detectors 8 and 10 are normally conveyed through "constant-fraction" discriminators (CFD) 21. If suitable detectors are chosen, the CFDs 21 may be unnecessary.

The pulses are then fed to a "time-to-amplitude" converter (TAC) 22. A TAC converts the time difference between a starting pulse and a delayed stopping pulse applied thereto into a voltage amplitude. A starting pulse starts a substantially linear voltage slope, the subsequent rise of which is interrupted on arrival of the stopping pulse. The voltage reached hitherto is delivered at the output. In order to determine the time interval between the laser excitation pulse and the time of detection of the photon, the trigger signal of the laser pulse will first be supplied to the TAC starting input and the electric pulse from the detector 8 which detected the photon will be supplied to the stopping pulse (so-called normal mode). The time interval between excitation of the target particles and emission of the photon can therefore be determined, apart from constant delays.

Not every photon emitted from the sample space can be detected by the microscope objective 3 and the detector 8. It is possible for only about 1%. Consequently the excitation pulses of the laser 20 are much more numerous than the detected photons. In order nevertheless to obtain reliable determination of properties, the maximum number of detected photons is needed. The number of detected photons can be between e.g. 50 and e.g. 50 million. The number of excitation pulses must be correspondingly higher.

If a corresponding histogram is prepared from the determined delay times, the decay in time of the fluorescence will be found reconstructed as a curve in the histogram.

To avoid an unnecessary load on the TAC 22 and consequent idle time, the pulse from the detector 8 indicating a detected photon is applied to the starting input of the TAC 22 and the trigger pulse from the laser 20 is applied to the stopping input of the TAC 22 (so-called inverted mode). This effectively corresponds to a reversal of the time direction. The original signal can be reconstructed without difficulty by re-reversing the time direction and by optional constant displacement of the time axis in the downstream computer unit.

The output voltage from the TACs 22 is fed to an analog-digital converter (ADC) 23. The digitised amplitude value is then fed through a line 12 to a digital input/output card 28 and thus conveyed to a computer 27, where a multi-channel analysis is usually made in order to construct the histogram. The histogram is thus built up from the individual digitised amplitude values, each representing the delay time of a detected photon.

The known arrangement described hitherto can only determine the delay time of a detected photon. It cannot determine the absolute time when the photon was detected, i.e. since the beginning of the measurement, relative to a fixed reference point or relative to the time when the last photon was detected. To achieve this, various components have been added to the previously described arrangement and will be explained in detail hereinafter.

In a first exemplified embodiment an enquiry pulse output by the ADC 23 after each conversion is fed via a line 11 firstly to a change-over device 24 and then to the digital input/output card 28 for triggering a data recording. The enquiry pulse switches over the outputs of the change-over device 24, which is so constructed that it switches over on the rising flank of the enquiry pulse and thus effectively halves the frequency thereof. It thus constitutes a frequency-divider circuit. A frequency-divider circuit 24 is based on a flip-flop and has two outputs which in conventional manner are negated relative to one another. It can be constructed in known manner out of D or JK flip-flops.

The first output 15 of the frequency divider 24 is coupled e.g. to the stop input of the first counter 17 and the start input of the second counter 18. Correspondingly the second output 16 of the frequency divider 24 is coupled to the start input of the first counter 17 and the stop input of the second counter 18. The reverse connection would be equally suitable.

The frequency-divider circuit 24 after receiving an enquiry pulse from the ADC 23 can e.g. start the first counter 17 and stop the second counter 18. The first counter thereupon counts cycles of a clock generator 25 shown in FIG. 1.

The clock generator 25 can be e.g. a conventional quartz clock, the frequency of which is variable by inserting certain jumpers. Typical frequencies for the clock generator 25 are between 100 MHz and 20 kHz. The trigger signal derived by the laser 20 itself from the detector 10 can also be used as a clock.

After another photon has been detected by the detector 8, another enquiry pulse is triggered by the ADC 23. The frequency divider 24 thereupon switches its outputs over and the first counter is stopped and the second counter is started. The stopped first counter thereupon transfers its count to an intermediate memory 26. The enquiry pulse is fed from the frequency divider 24 through a second line 11 to the digital input/output card 28. Similarly the contents of the intermediate memory 26 are fed through a line 13 to the input/output card 28.

After reception of the enquiry pulse, the digital input/output card 28 is ready to record data. It thereupon records the converted TAC value output by ADC 23 via line 12 and also the contents of the intermediate memory 26 via line 13 and stores them together in the computer 27.

The converted TAC value typically has a width of 8 bits and the intermediate memory 26 has a width of 24 bits, so that the digital input/output card 28 should have an input width of 32 bits. Other bit widths are of course also suitable, provided the frequency of the clock generator 25 and the width of the intermediate memory 26 are adapted to the experimental conditions. 64-bit accepting input/output cards can also be used. Different bit ranges can be reserved for the signals from different detectors. Likewise individual bits can be used to code the detector which has detected a particular photon.

At the end of the data recording the input/output card 28 delivers a confirmation signal through line 14 to the analog-digital converter, which is then ready for a new conversion.

If a third photon is detected by the detector 8, the ADC 23 sends another enquiry pulse through line 11 and the frequency divider 24 switches over its outputs again. The first counter is then re-started and the second counter is stopped. The second counter then transfers the contents of the intermediate memory 26 and the said contents are received by the input/output card 28 via line 13. The same happens in all subsequent photon detection events.

In this manner the time interval to the next excitation pulse and the time interval from the preceding time of detection is stored for each photon.

Both items of information are suitable for evaluation either together (see the method according to the invention hereinafter) or separately. If for example only the time of detection of photons is of interest, the digitised TAC values can be disregarded and the times of detection can be supplied for suitable evaluation. If on the other hand only the time sequence of fluorescence decay is of interest, the converted TAC values can be combined in a histogram and evaluated without further consideration of the time intervals between the times when individual photons are detected.

Figure 2:
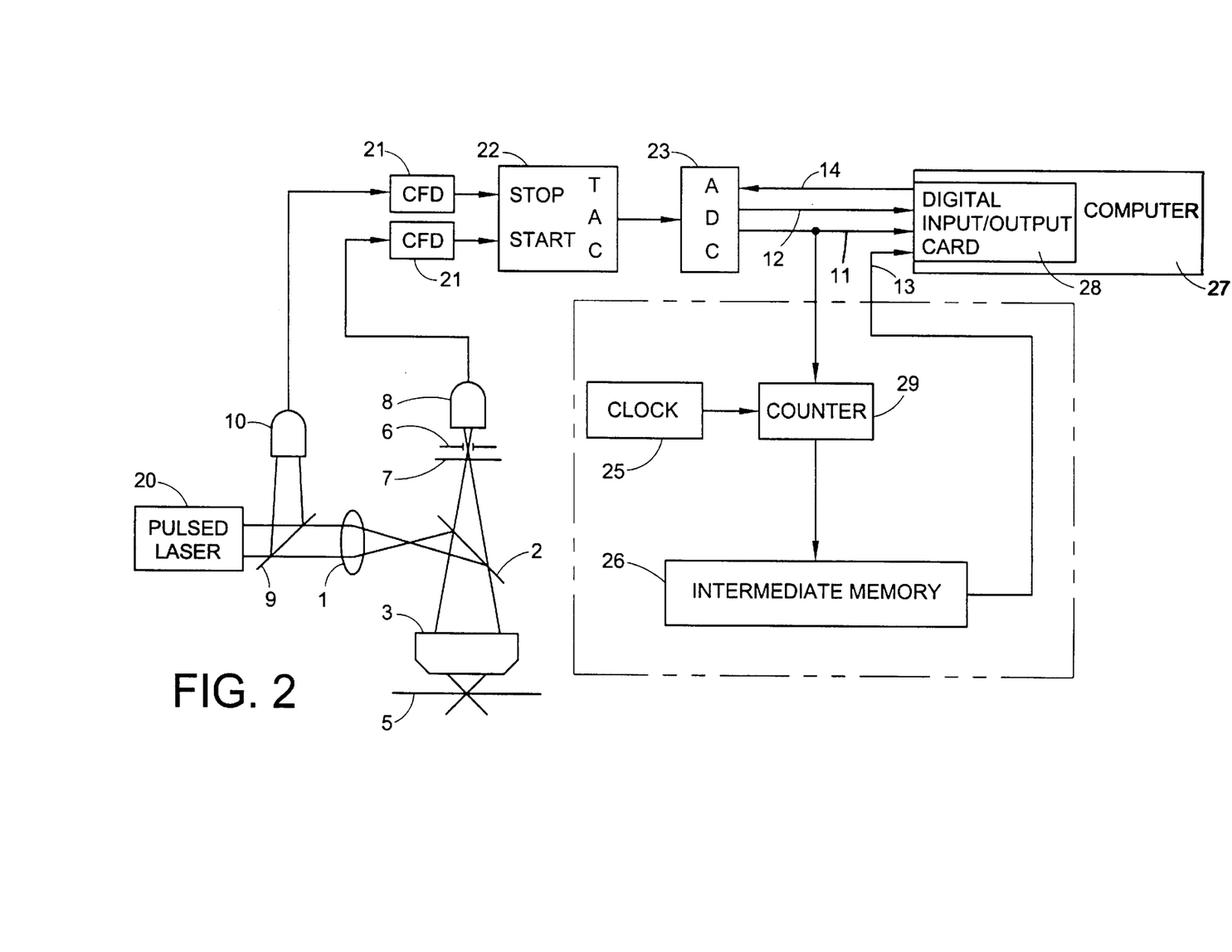
FIG. 2 is a block diagram of a second exemplified embodiment of the invention.

In another exemplified embodiment, instead of an alternating counter arrangement only a single counter or clock is used as shown in FIG. 2, which will now be referred to.

An enquiry pulse of the ADC 23 output through line 11 causes the intermediate memory 26 shown in FIG. 2 to detect and temporarily store the time shown by the counter 29 or clock. The resulting contents of the intermediate memory 26 are received by the digital input/output card 28, after receiving an enquiry pulse via a line 13, in the same manner as described in the first embodiment.

In a third embodiment the counter 29 is connected as in the second embodiment so that an enquiry pulse from the ADC 23 stops it. The actual count is written in the intermediate memory 26 and the counter 29 is reset and begins to count afresh. The contents of the intermediate memory 26 are recorded by the digital input/output card 28 together with the digitised TAC value via the line 12, after the digital input/output card 28 has received the enquiry pulse from the ADC 23 via line 11, as already described in the first embodiment. The bit width of the intermediate memory 26 and of the ADC value can be constructed in the same manner as described in the first embodiment.

In this embodiment also, the counter 29 counts cycles e.g. of the clock generator 25 shown in FIG. 2, which can be constructed with a variable clock rate as in the first embodiment.

The arrangements described in the embodiments can be constructed so that the counters, intermediate memories, clock generators and clocks are outside the computer 27 and the data are received in the computer 27 via the digital input/output card 28. Alternatively all the components of the arrangements can be disposed on a printed circuit board and integrated in the computer 27.

In a fourth embodiment the pulses from the detectors 8 and 10 or the CFDs 21 are not effectively processed for the computer 27 by a TAC 22, an ADC 23 and the previously described other components. Instead the analog variation in time of the signals is detected with maximum accuracy in time. This can be done e.g. by using a double-beam oscilloscope with maximum storage depth. The resulting data can then be converted into delay times and intervals between detection times.

After the preceding description of the arrangements according to the invention we shall now describe how the properties of the target particles are determined from the acquired data.

Figure 3:
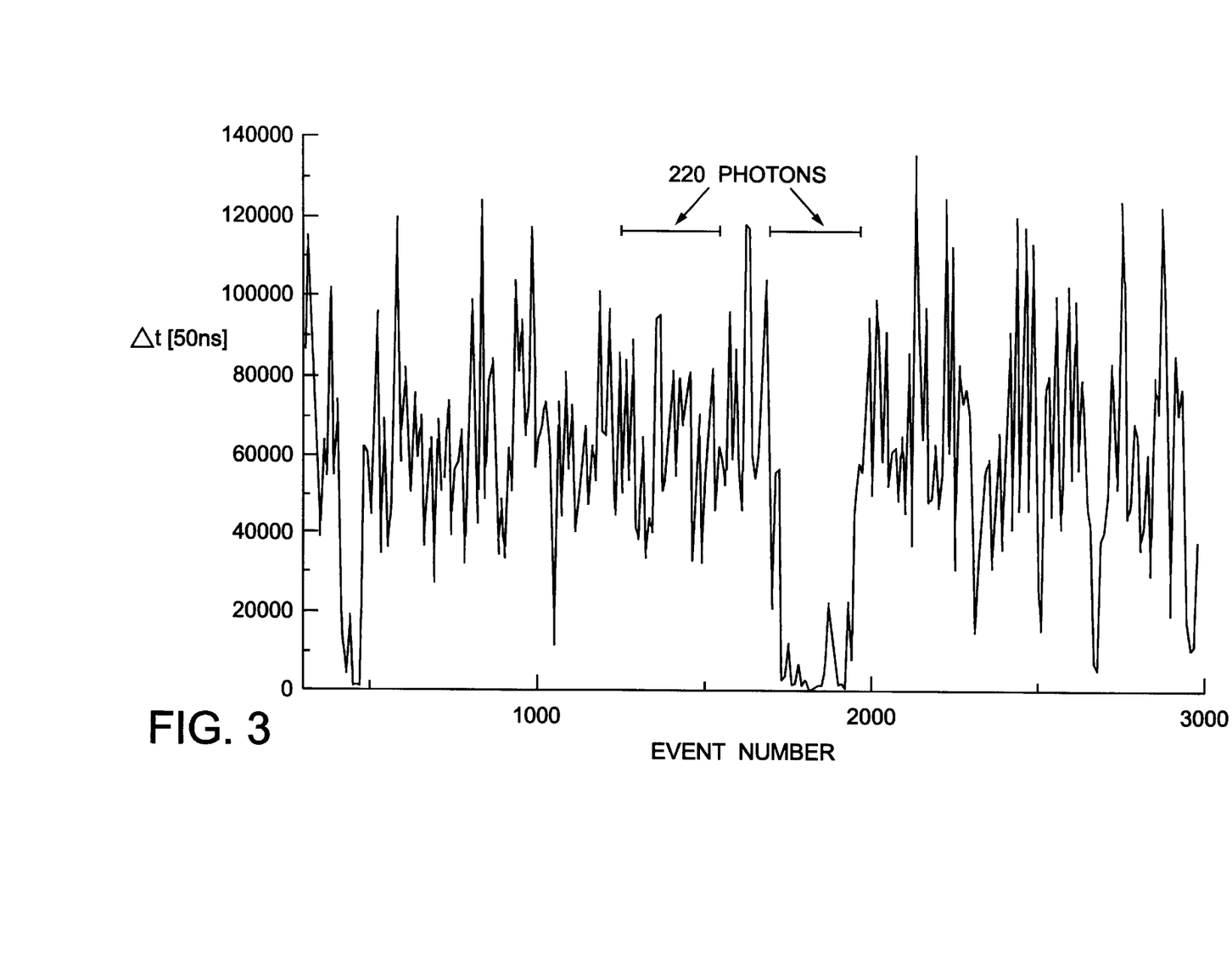
FIG. 3 shows a curve which describes the time intervals $\Delta t$ between successive times of detection of photons in a photon sequence.

Reference will now be made to FIG. 3. FIG. 3 shows a curve which describes the time intervals Δt between successive times of detecting photons in a photon sequence. The photons are numbered in order of detection and plotted on the X axis with the event number. The time interval between detection of successive protons is here detected with an accuracy of 50 nanoseconds, corresponding to a clock rate of 20 MHz in the clock generator 25. This measurement is made with a confocal structure. The target particles used are rhodamine-110 dye molecules dissolved in ethylene glycol.

If no target particles or rhodamine-110 molecules are present in the sample space, the rate at which detected photons are counted is much lower than when a highly absorbent and fluorescent dye molecule such as rhodamine-110 is in the volume element under observation. Examples thereof are shown in FIG. 3. Around event No. 1500 approximately, the time interval between individual photon detection events is about 60,000×50 ns, i.e. about 3 ms, corresponding to a background counting rate of about 300 Hz. At event No. 1900 approximately the time interval between detection times of individual photons is much smaller. The average interval between individual photon events in the second case is in some cases about 1000×50 ns, i.e. about 50 μs. This corresponds to a detection rate of about 20 kHz. It is therefore about 60 times greater than the background counting rate.

Figure 4:
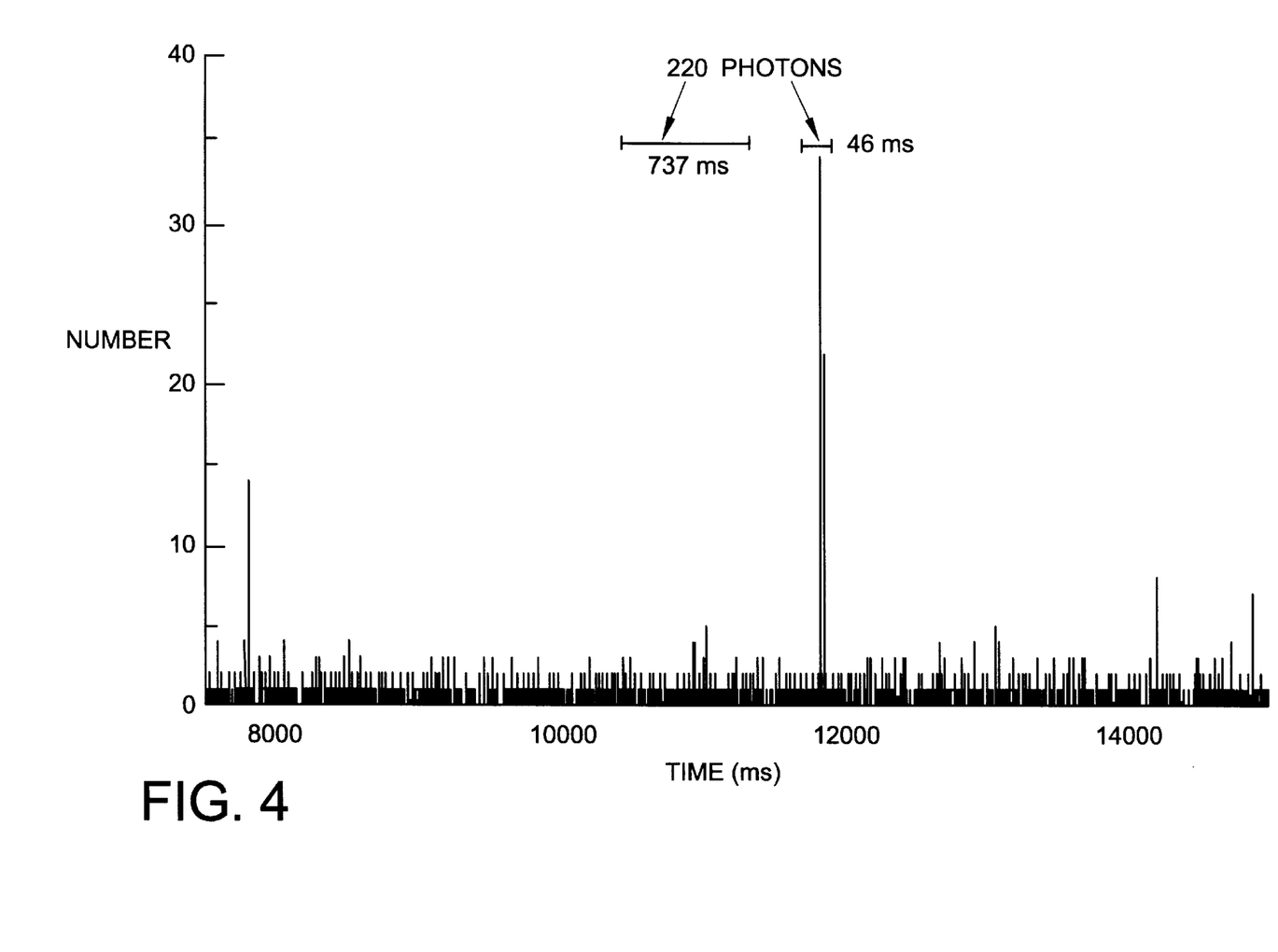
FIG. 4 is a histogram in which the number of photons detected per unit time is plotted in the case of the photon sequence in FIG. 3.

This can be seen directly from the diagram in FIG. 4, which will now be referred to. FIG. 4 shows the data of FIG. 3, except that it is not the time interval between detection of successive photons but the number of photons detected per millisecond that is plotted along the Y axis. Also the event number on the X axis is replaced by the time. FIG. 4 can be obtained from the data at the basis of FIG. 3 by adding the time intervals between the individual detection times and thus associating each photon with the absolute time when it was detected. The number of detection times occurring in each millisecond interval can then be determined and plotted. In FIG. 3 two regions each corresponding to 220 detected photons are marked. The same regions are plotted in FIG. 4. The region around the event number of about 1500 approximately in FIG. 3 takes 737 ms in FIG. 4. The same number of 220 photons around the event No. 1900 in FIG. 3, which correspond to a much higher average detection rate, takes only 46 ms in FIG. 4. As can be seen, the photon detection rate is increased by the fact that a rhodamine-110 molecule is in the focus or the sample space. The result in the illustration in FIG. 4 is a peak which rises distinctly above the background.

The method of representation in FIG. 4 is usually described as multi-channel scaling (MCS) or multi-channel counting.

A measuring process which generates data in the form in FIG. 4 (MCS measuring processes) illustrates the determination of an individual molecule, whereas a method of measurement which records data in the form in FIG. 3 is a more accurate method of evaluating data. This is because in FIG. 3 each individual photon can be allotted the exact time when it was detected. In MCS measuring processes, on the other hand, the time when a photon is detected is frequently determined with an accuracy of only 1 ms.

Typical diameters of the sample chamber or focus in a confocal structure are between 0.5 and 1 μm. The time needed for a rhodamine-100 molecule to diffuse through a distance of 0.5 μm, i.e. to go through the focus, has an arms value of about 500 μs. An integration-time channel width of 1 millisecond is therefore near the transit time of the molecules through the focus. MCS data therefore cannot be used for more accurate investigation of entry and exit times. Such data are needed, however, in order to calculate correlation functions for the recorded data. This will be explained in further detail hereinafter.

In order to decide whether a target particle is in the focus during a measurement interval, consideration can be given either to the photon detection rates shown in FIGS. 3 and 4 or to the respective decay behaviour of the detected signal on an ns scale for the individual measurement intervals. In that case, in the usual manner for time-correlated single-photon counting, the time interval between the laser pulse or excitation time and the time when the photons are detected, i.e. the fluorescence delay time, is shown in histogram form for the individual photons during the measurement interval. This is shown in FIGS. 5 and 6 for examples of data from FIGS. 3 and 4.

Figure 5:
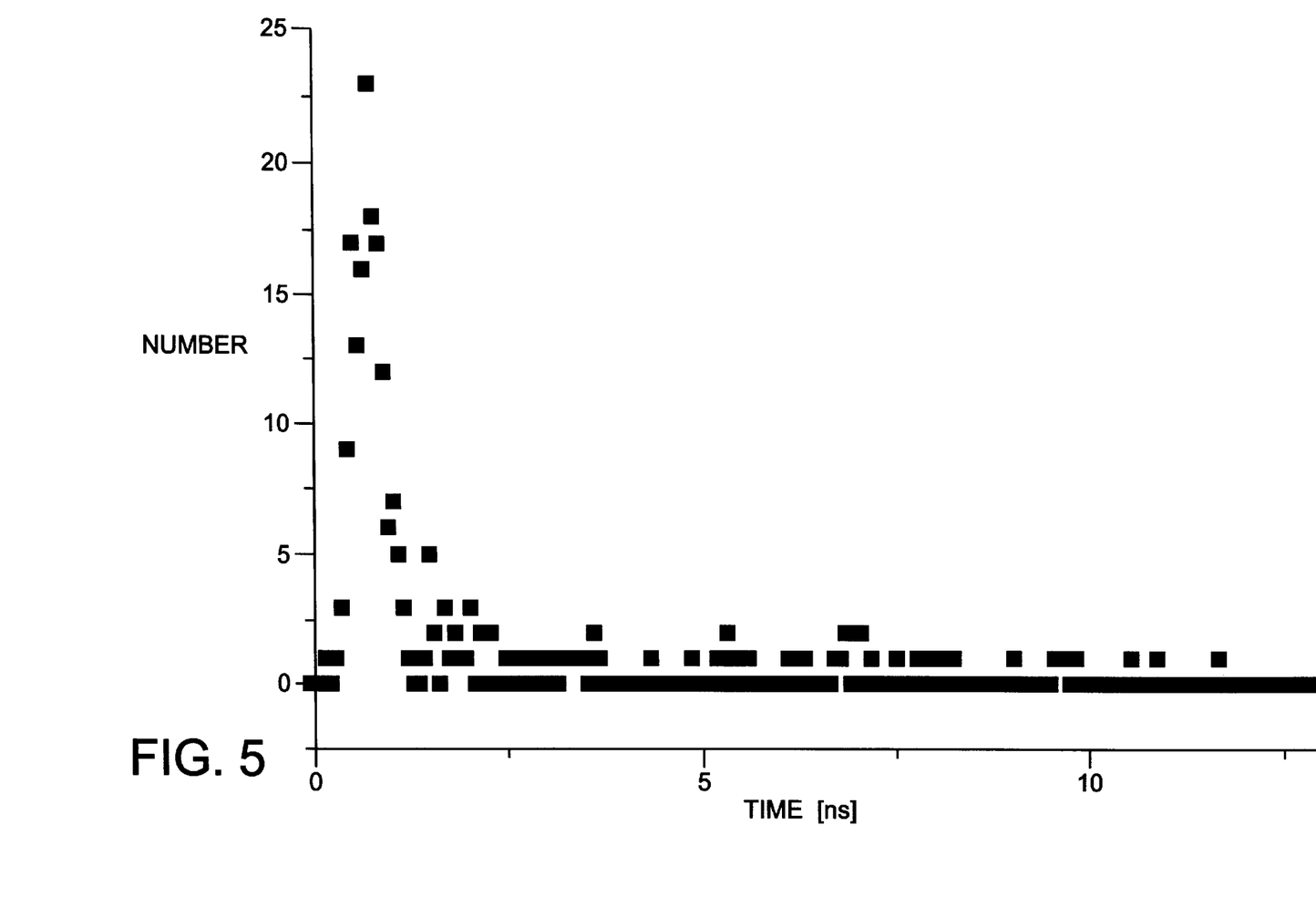
FIG. 5 is a histogram obtained from the time intervals between excitation pulses and times of detection of photons, in the case of a first interval marked in FIGS. 3 and 4.
Figure 6:
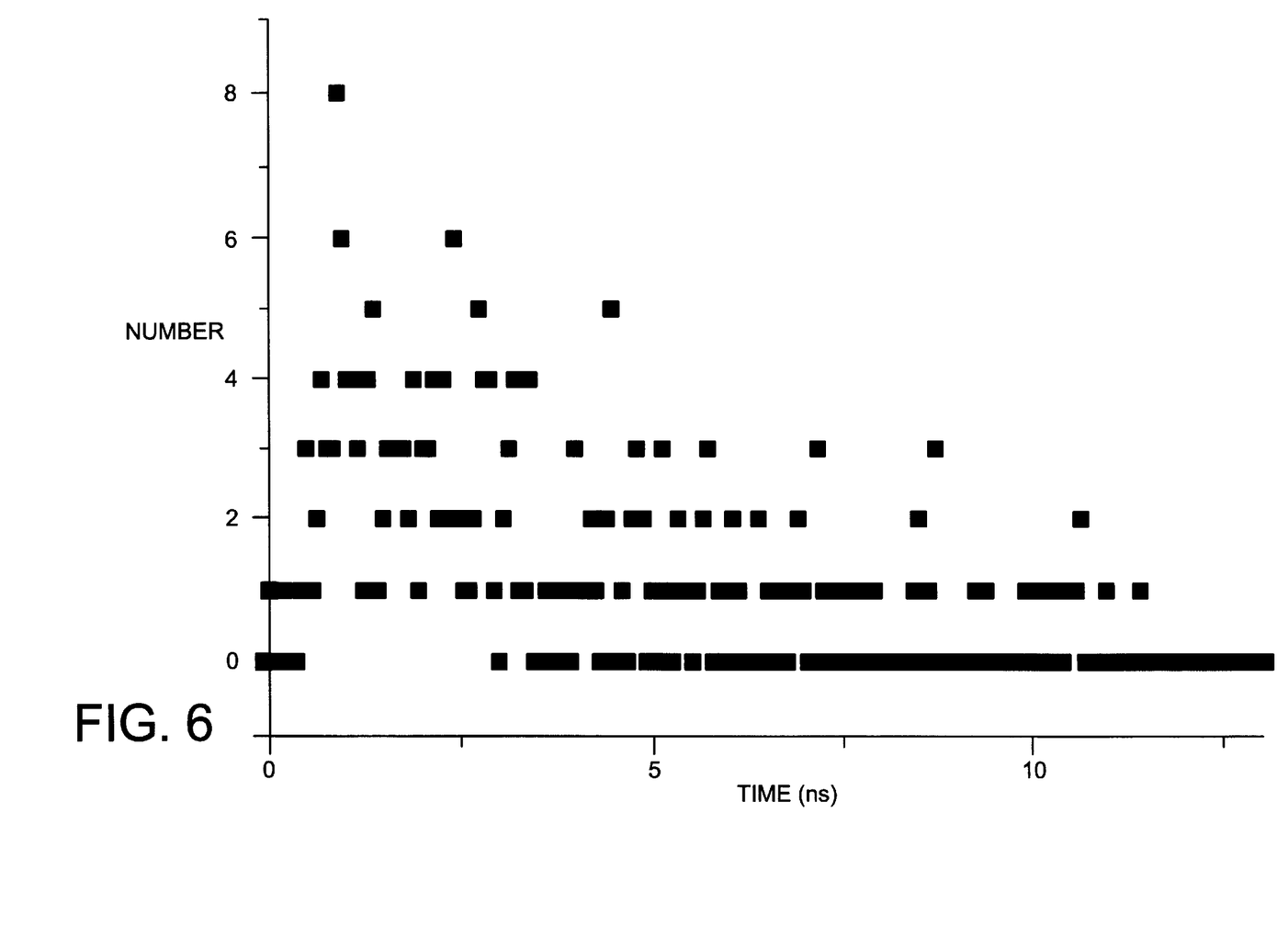
FIG. 6 is a histogram obtained from the time intervals between excitation pulses and times of detection of photons, in the case of a second interval marked in FIGS. 3 and 4.

The histograms in FIGS. 5 and 6 were prepared with a time resolution of about 50 picoseconds per channel.

For each photon, the distance in time from the preceding time of detection of a photon is stored together with the associated delay time. These values are always below the period of the exciting light or the time interval between successive laser pulses. In FIGS. 5 and 6 the delay time is between 0 and about 12 ms.

FIG. 5 shows a histogram of this decay behaviour in time in the case of the region of 220 photons marked in FIG. 3 around event No. 1500 approximately and for the region of 220 photons marked in FIG. 4 and corresponding to 737 ms. As shown in FIGS. 3 and 4, no target particle is in the sample space during this measurement interval. Accordingly FIG. 5 shows a histogram time curve which has a peak at an early moment followed by an almost uniformly distributed time curve. The peak corresponds to non-delayed scattered light and the almost uniformly distributed subsequent curve corresponds to other background noise.

In contrast thereto FIG. 6 shows the time curve of the fluorescence of a rhodamine-110 molecule or target particle. FIG. 6 shows a histogram of the kind in FIG. 5 for the region of 220 photons marked in FIG. 3 around event No. 1900 approximately and for the region of 220 photons marked in FIG. 4 and corresponding to 46 ms. As already clear from FIGS. 3 and 4, a target particle or rhodamine-110 molecule is in the focus during this measurement interval. Correspondingly the time curve of fluorescence shown in FIG. 6 has an initial steep rise corresponding to excitation by the brief laser pulse and then decreases substantially uniformly. The decrease per unit time is much slower than in FIG. 5. The fluorescence life inferred from FIG. 6 is in the neighborhood of 3.6 ms.

In addition FIG. 6 at the beginning shows a pronounced peak, which can originate from additional non-delayed scattered components of the scattered light. In order to decide whether the initial peak—and comparable peaks in comparable histograms—is due to additional non-delayed scattered components of the scattered light, non-delayed scattered light only is recorded in separate measurements, e.g. in pure ethylene glycol. The resulting time curve is comparable with FIG. 5 but with significantly higher numbers of detected photons per channel of the histogram.

The fluorescence decay behaviour of target particles rhodamine-110 in this case—can be detected similarly in separate measurements.

These previously known data can then be used to decide the proportion of non-delayed scattered light to the amplitude of the data e.g. in FIG. 6. This can be done by efficient statistical algorithms, e.g. a least-square adaptation or a maximum-likelihood adaptation as described in the literature (see e.g.: J. N. Demas: "Excited state lifetime measurements", Academic Press, New York, 1983, or M. K öllner, J. Wolfrum, Chemical Physics Letters, Volume 200 (1992), pages 199–204).

The fluorescence life can be determined with greater accuracy, allowing for the proportion of non-delayed scattered light, by an adaptation test, assuming e.g. an exponentially falling curve for the decay in fluorescence of the target article and a yet to be determined proportion of non-delayed scattered light in the signal. This therefore is a method of determining the fluorescence life of a target particle as a predetermined property of the target particle, using the measured amplitude components, i.e. the fluorescence and the non-delayed scattered light in this case. Other components e.g. from other particles or other scatter sources can be taken into account via similar separate measurements and the data obtained therefrom.

To increase the efficiency of detection, the optical structure shown in FIGS. 1 and 2 can be supplemented by a second microscope objective in line with the ray path of the first microscope objective 3 underneath the sample-holder 5. The light-collecting efficiency is doubled as a result. The microscope objective, like the microscope objective 3, must be followed by a filter, a pinhole and a detector. The other downstream data-acquisition electronic unit and evaluating device can be installed separately for the second detection path, or the signals from the second detector can be fed to the existing TAC 22 via a routing unit. In the first-mentioned case (a separate data acquisition arrangement) the photons detected at the individual detectors can be individually evaluated in the manner described. More particularly, the amplitudes of the individual scattered-light components, i.e. of the delayed scattered light or fluorescence and the non-delayed scattered light, can be determined for the photons detected by the individual detectors and the properties of the target particles can be calculated therefrom. The data can also be combined in the appropriate histograms and evaluated all together.

The efficiency of detection can be further increased by using a suitable mirror directly underneath the sample.

The histograms in FIGS. 5 and 6 were prepared for a measurement interval in which 220 photons were present. Any other suitable number of photons could equally well be combined in a histogram. It is also obvious from FIG. 4 that histograms as in FIGS. 5 and 6 can be prepared not for a given number of photons but for a given predetermined time interval.

In the case where the intervals are defined by a predetermined number of detected photons, a sliding evaluation for various photon portions in FIG. 3 can be obtained by forming and analysing suitable histograms. For example, a subsequently detected photon can be incorporated in the histogram and a previously detected photon can be removed. Alternatively, instead of one photon, ten or any other number of photons can be included or removed from the histogram. Also the predetermined number of detected photons can be varied. For example in the case where single target particles are present, the number can be made larger or smaller than in the case of other scattered light.

The determined amplitude components of the individual scattered-light components or if required the determined life can then be plotted against time or the event number, via times of detection or the time intervals between successive times of detection. This is shown by way of example in FIG. 7.

Figure 7:
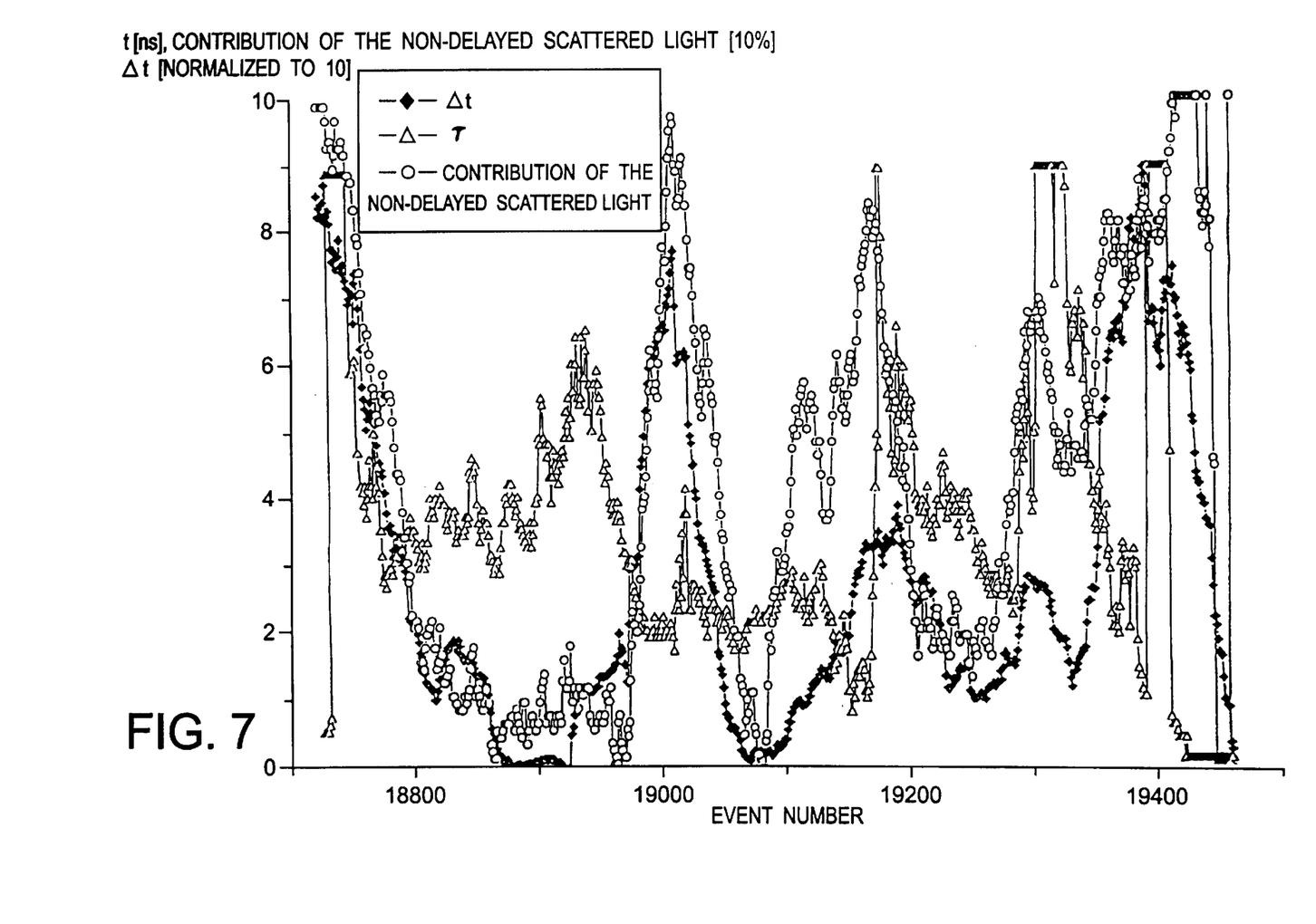
FIG. 7 is a family of curves showing an example of evaluation of recorded data.

FIG. 7 shows a sliding evaluation of data based on FIG. 3, the histograms each being prepared on the basis of 40 photons and each next histogram being prepared by adding a subsequently detected photon and leaving out a previously detected photon. The interval marked Δt between individual times of detection of photons, marked "♦" in FIG. 7, is likewise averaged over 40 photons.

The region around event No. 18850 approx. shows very clearly that a small time interval of detected photons, indicating the presence of a target particle in the focus, is correlated with a similarly small amplitude component of the non-delayed scattered light and a long fluorescence life. In this case the fluorescence life is about 4 to 5 ns. By contrast, the region around event No. 19000 approximately shows a long time interval between successive photon events, i.e. no target particle is in the focus, and consequently the amplitude component of the undelayed scattered light rises to nearly 100% and there is a marked decrease in the fluorescence life.

Data in the form shown by way of example in FIG. 7 are also suitable according to the invention for further processing. In the literature (e.g. M. Eigen, R. Rigler, Proceedings of the National Academy of Sciences of the U.S.A., Vol. 91 (1994), pages 5740–5747) there is a general description how, via the autocorrelation function of the detected photons, it can be reliably decided whether only one target particle or more than one target particle on average was in the focus during the measurement. Also the diffusion constant of a target particle can be calculated from the autocorrelation function of the scattered light. Correlation functions can also be used to determine the significant common presence of individual components of the scattered light. To this end the cross-correlation function of the individual determined amplitude components is calculated in known manner. If the function has a pronounced peak around the time zero, the scattered-light component under consideration occurs significantly simultaneously in the signal or usually occurs simultaneously. This enables the occurrence together of two target particles to be significantly shown.

A measurement of this kind is of interest whenever bonding between two molecules or molecule complexes has to be demonstrated for pharmacological purposes. This may be relevant in "drug screening" where it is frequently of interest to demonstrate a particularly strong bond between a target particle, e.g. an antigen, and another target particle, e.g. an antibody. If the target particles between which a bond is to be observed are both fluorescence-labelled, the respective amplitude components should simultaneously take high values. The amplitude components can be determined e.g. via the data recorded separately for these target particles. If the bond is weak, the simultaneous occurrence will be only weakly marked. If the bond is strong, the particles are usually bonded to one another and are therefore observed simultaneously in the focus.

Bonding can also be demonstrated by a sandwich test. In a sandwich test the bonding of a desired molecule between two other molecules is observed. At least one of these molecules must be fluorescent or fluorescence-labelled. If both are fluorescence-labelled, their occurrence together can be determined via a correlation function and used for quantitative analysis of the bond. If only one of them is fluorescent, bonding can be inferred from the autocorrelation function, via a changed diffusion constant.

Since the method according to the invention can be used to investigate single particles, it is not only a means of detecting the average value of physical measurements. On the contrary, the distribution of the measured value can be directly measured by determining a number of individual measurements on individual target particles. By this means, the heterogeneity of a heterogeneous quantity of target particles can also be analysed.

According to the invention, for example, the autocorrelation function of the fluorescence lives can be shown as a specific parameter. The autocorrelation function of the proportion of scattered light due to fluorescence of the target particles can also be calculated. This amplitude component, as already explained, can be determined by taking account of the known fluorescence life of the target particle. The result is a selective fluorescence life autocorrelation function, from which an associated diffusion constant, for example, can be calculated.

By contrast to conventional FCS techniques, the correlation function according to the invention can be calculated selectively, eliminating scattered-light components. The result is an improved signal-to-noise ratio for an extremely weak signal which results from target particles which are rarely and singly present in the sample space.

A selective fluorescence-light autocorrelation function can be used e.g. for quantitative analysis of the bonding of a fluorescent target particle whose fluorescence life is different in the bonded from in the free state. "Intelligent" dyes described e.g. in DE-OS 38 07 975 are suitable dyes for this purpose. In this case according to the invention the autocorrelation function can be calculated selectively for the bonded and for the free state.

The cross-correlation function of different parameters can also be calculated, so that the significant common occurrence or significant separate occurrence at a peak or trough can be read off around the time zero of the cross-correlation function.

In the case of two detectors also, the cross-correlation function can be calculated for similar or different parameters, specified for the data from the individual detectors. As before, information can be read off about common or separate occurrence of target particles.

It may also happen that more than one target particle is in the focus. If different target particles have different fluorescence lives, the measured signal converted into a histogram can have a multi-exponential time curve of the decay in fluorescence. The fluorescence curve can be of this kind if the individual target particles already have a multi-exponential decay in fluorescence. In that case the previously mentioned statistical methods can be used by determining a separate amplitude component for each individual exponential decay. To do this appropriately, data about the fluorescence decay of the various target particles or of each individual target particle are recorded in separate measurements as before.

In the case of multi-exponential fluorescence decay or in the case where more than one target particle is present in the focus, the fluorescence lives of the individual target particles can be determined in addition to the amplitude components thereof relative to the total scattered light, insofar as the different target particles have different fluorescence lives. Also these amplitude components or fluorescence lives can be correlated with one another or their cross-correlation function can be calculated. The occurrence together of target particles, e.g. bonded to one another, can be demonstrated by simultaneous occurrence of the elevated amplitude components or fluorescence lives. The "multiplex" dyes described in DE 42 10 970 C2 are particularly suitable for this purpose.

The spectroscopic data can also reflect the rotational properties of the target particles, as universally known in spectroscopy. Rotation of a target particle results in depolarisation of fluorescence during the decay time. This depolarisation behaviour can be determined in a histogram as in FIG. 6, by using polarised exciting light and an analyser in front of the detector 8. If the depolarisation behaviour is accurately determined in separate measurements, knowledge thereof can also be used to determine the fluorescence amplitude component of a target particle as a proportion of the total scattered light.

In addition to spectroscopically independent fluorophores e.g. for the two target particles mentioned hitherto, use can also be made of two fluorophores between which a resonant energy transfer occurs. For example, the first target particle can be simulated by the laser light, i.e. can absorb laser light, the energy can be resonantly transmitted to the second target particle, and the latter particle can emit. Resonant energy transfer of this kind is closely dependent on distance, i.e. it will occur efficiently if the target particles are bonded to one another and will be practically absent if the target particles are not bonded together. If the amplitude components of the individual target particles in the scattered light are then determined and their cross-correlation function is calculated, a strong bond between the target particles will be shown by the fact that only the fluorescence of the second target particle, which receives the transmitted energy, is observable when both occur simultaneously in the focus. A negative correlation in the cross-correlation function will then be observed.

The curve of an autocorrelation function for scattered light recorded by the previously described confocal optical structure is determined by the diffusion of the fluorescent particle. The characteristic quantities for it are the diffusion constant of the particle and the spatial dimensions of the focus. These diffusion constants also critically influence the cross-correlation functions previously described. The diffusion constants of the individual target particles and the characteristic curve of their autocorrelation function can be determined in separate measurements. By means of this knowledge, the cross-correlations can be evaluated to show the proportions of the individual target particles in the production of the correlation functions.

As already mentioned, the arrangements according to the invention are particularly suitable for spectroscopic investigation of individual target particles. In order to decide if or that an individual t-target particle is in the sample space or medium or the volume under observation, the target particles must first be present in a dilution such that on average there is less than one target particle in the observed part of the sample medium or in the sample space. Typical concentrations for this purpose are $10^{-9}$ to $10^{-12}$ M solutions (M=mol/litre). If for example a $10^{-12}$ M solution of rhodamine-110 in ethylene glycol is used and the focus is elliptical with a minor semi-axis of 0.25 $\mu$m and a major semi-axis of 2.5 $\mu$m, the volume of the observed sample space will be about 0.65 $\mu m^3$. Multiplication by a concentration of $10^{-12}$ mol/litre of rhodamine-110 molecules gives a probability of about $4 \times 10^{-4}$ that a rhodamine-110 molecule will be in the sample space under observation at a given time.

More highly concentrated solutions can also be investigated if the fluorescence behaviour of the target particle present in very dilute form in the said solution is influenced by the more highly concentrated particles. The influence is via local molecular interactions and can affect the fluorescence life and other characteristics of the fluorescence behaviour such as the intensity of fluorescence, the depolarisation behaviour or the like. The depolarisation behaviour may alter e.g. as a result of bonding between the target particles and the more highly concentrated particles.

The fluorescence behaviour of the target particles determined under these conditions will give information about the more highly concentrated particles. The target particles may be so highly diluted that single particles are usually present in the sample space.

FIG. 3 will now be considered again. The relatively small time intervals between the detected photons at event No. 1900 approximately and the correspondingly relatively high density of times of detection, i.e. the high detection rate of photons, indicate the presence of a single target particle in the sample medium as already explained. For more quantitative treatment, use can be made of the averaging and threshold-setting process described in R. A. Keller, Applied Spectroscopy, Volume 50, No. 7 (1996), pages 12A to 32A.

Alternatively any parameter which can be determined from the histograms, e.g. the amplitude component of a given fluorescence life, can be used e.g. via simple threshold-setting processes for deciding whether an individual target particle is present in the sample space.

Also use can be made of a statistical process which tests the hypothesis whether the observed signal can originate from pure background noise. To this end the probability is calculated of observing a number of photons in these short time intervals, assuming that they originate from background noise or non-delayed scattered light. If this probability falls below a predetermined value, at least one fluorescent molecule or target particle is present with corresponding significance in the focus.

If, as in FIGS. 3 to 6, the photons associated with an individual target particle present are selected and a histogram is constructed as in FIG. 6, the fluorescence life for an individual target particle can be determined. Alternatively the observed decay in fluorescence can be compared with known data for particular kinds of target particles, and it can be decided which of the known kinds of target particles are present in this case. Algorithms described by M. Köllner in Applied Optics Volume 32 (6) (1993), pages 806 to 820, are particularly suitable for this purpose. Individual molecules or target particles can be identified in this manner.

The arrangements for data acquisition and the associated methods of evaluation are thus suitable for the methods described in DE 42 10 970 C2 for optical qualitative and quantitative determination of biomolecules etc. by laser spectroscopy. This is particularly the case when the arrangements and methods described here are applied to individual target particles present.

Also one of the previously described methods of evaluation can be used to find whether a single target particle is present in the observed sample space. The data are then evaluated only if the corresponding algorithms have resulted in the decision that a single target particle is with high probability present in the sample space. This procedure is a form of sliding pre-evaluation.

Alternatively, the proportional amplitude of non-delayed scattered light to the total scattered light can be used for pre-filtering the data for subsequent evaluation.

More particularly, the pre-filtered signals can be used for efficiently calculating the autocorrelation function of the detected photons for individual target particles present. To this end the autocorrelation function is constructed only from protons detected at times when a single target particle was present with predetermined probability in the sample space. Such photons, associated with the general undelayed scattered light and the rest of the background, are not included in the calculation. This results in effective suppression of scattered light and a corresponding improvement in the accuracy and amplitude of the calculated autocorrelation function, since the amplitude of the autocorrelation function depends on the signal-to-noise ratio of the function on which the autocorrelation is based. The poorer the ratio, the lower the amplitude of the autocorrelation function (compare D. E. Koppel, Physical Review A, 1974, Part 10, page 1938).

If exclusive use is made of the information available at the time of detection of the photons, without using the information from the delay times, a correlation function by itself can be calculated for the times of detection of photons associated with individual target particles, instead of for parameters determined therefrom.

In contrast to conventional FCS, as already explained, this results in a marked improvement in the signal-to-noise ratio. The correlation function can be selectively calculated for the individual target particles.

Any kind of light can be used for this application, particularly continuous light which is not modulated.

In order to decide whether a single target particle is present in the sample space, according to the invention use can be made of a relatively high density per unit time, or of relatively short time intervals between the times when successive photons are detected. As already described, this is clearly recognisable in FIG. 3 around event No. 1900 in conjunction with FIG. 4. The "troughs" in FIG. 3 appear in FIG. 4 as peaks, which can generally also be described as "bursts".

A comparison between the relatively short time interval between the times of detection of successive photons around event No. 1100 in FIG. 3 and the trough in the curve around event No. 1900 shows that troughs vary greatly in duration or are made up of widely different numbers of detected photons. In order to judge whether a trough of this kind is due to random fluctuation in the background signal or to an individual target particle present, use can be made of the previously mentioned statistical criteria, which would identify the trough around event No. 1100 as originating from other scattered light.

Consequently, assessment of the duration of a burst is also an efficient method of assessing whether a relatively high density of times of detection of photons indicates the presence of a target particle.

Numerous variations can be made within the scope of the principle of the invention. In principle, the presence of a single target particle can be detected if a parameter is above or below a specific value (compare FIG. 7) or the number of times of detection per unit time (intensity) can be used (compare FIG. 4). There are therefore two basic methods of threshold-setting. In addition, either a correlation function of a parameter or a correlation function of the intensity can be calculated. The two possibilities of thresholdsetting and the two possibilities of calculating correlation functions result in a total of four possible combinations, i.e.:

1. A threshold for the intensity can be predetermined and a correlation function of the intensity can then be calculated.
2. A threshold for the intensity can be set and a correlation function of a parameter can then be calculated.
3. A threshold for a parameter value can be predetermined and a correlation function of the intensity can then be calculated or
4. A threshold for a parameter value can be predetermined and a correlation function thereof or of another parameter can then be calculated.

The light source, the detection device and the evaluation device must be chosen in accordance with the individual possibilities as described.

It is thus possible for the first time, using the method and arrangement according to the invention, to carry out FCS even at very low concentrations, selectively for chosen target particles and with good signal-to-noise ratios.

What is claimed is:

1. A method of determining predetermined properties of target particles in a sample medium, wherein:
    a) the sample medium is irradiated with periodically modulated light having a predetermined period;
    b) light in the form of individual photons scattered in the sample medium is detected by a detection device;
    c) wherein the time interval between the time of detection of each photon and a reference time within the associated period of the irradiating light is determined and defined as the delay time;
    d) wherein the time of detection of each photon is determined in addition to determining the delay time of each photon, and
    e) wherein the delay times of detected photons are used to determine at least one parameter of the scattered light; characterised in that
        e') the at least one parameter is determined using the delay times for a respective number of immediately successive photons,
    f) a time value is determined using the times of detection of the respective number of immediately successively detected photons;
    g) at least one pair of parameter and time values is determined using the at least one parameter and the time value of the respective number of immediately successively detected photons;
    h) at least one parameter-time function is determined from the pairs of parameter and time values of a plurality of successive numbers;
    i) a correlation function of the at least one parameter-time function is calculated, and
    j) the predetermined properties of the target particles are determined by using the correlation function.

2. A method according to claim 1, characterised in that the periodically modulated light is modulated in pulses.

3. A method according to claim 1, characterised in that the light scattered in the sample medium is detected by more than one detector; and
    in that in each case at least one parameter-time function for the photons detected by each detector is calculated separately.

4. A method according to claim 3, characterised in that the correlation function is a cross-correlation function calculated by using the parameter-time functions of various detectors.

5. A method according to claim 1, characterised in that a histogram of the delay times is prepared for each predetermined number of successively detected photons of the scattered light or for a predetermined time interval, and
    in that parameters of the scattered light are determined from the histogram be efficient statistical methods.

6. A method according to claim 1, characterised in that the target particles are molecules capable of fluorescence or particles comprising groups (fluorophores).

7. A method according to claim 6, characterised in that the at least one parameter of the scattered light is determined allowing for the fact that the detected scattered light is made up of at least fluorescent light from the target particles and from proportions of other scattered light and
    in that the parameter determined is the proportion of the scattered light to the total amplitude.

8. A method according to claim 7, characterised in that the parameter determined is a fluorescence life.

9. A method according to claim 7, characterized in that in order to determine the proportional amplitudes of the individual components of the scattered light, predetermined information about the composition of the fluorescent light from the target particles is processed by superposing a number of individual exponential decays which can be described by specific fluorescence lives, and
    in that the parameters determined are the proportional amplitudes and/or the fluorescence lives of the individual exponential decays.

10. A method according to claim 9, characterised in that information about the typical fluorescence lives of the target particles is used in determining the proportional amplitudes of the individual exponential decays.

11. A method according to claim 7, characterised in that the proportional amplitudes of the light scattered by the respective target particles are determined by using information about the rotation or fluorescence depolarisation behaviour of the target particles.

12. A method according to claim 7, characterised in that the target particles used are at least two particles each comprising fluorophores, a resonant energy transfer occurring between the respective fluorophores;

in that the parameters determined are the proportional amplitudes of the light scattered by the respective fluorophores, and in that the correlation function determined is an autocorrelation function of the proportional amplitudes of the light scattered by the respective fluorophores.

13. A method according to claim 1, characterised in that the density of the target particles is so chosen that on average less than one target particle is present in an observed volume element of the sample medium (sample space) and in that the correlation function is calculated exclusively from portions of the parameter-time function associated with individual target particles.

14. A method according to claim 13, characterised in that the presence of an individual target particle in the sample space is ascertained when a predetermined threshold is exceeded by a predetermined parameter of the scattered light.

15. A method of determining predetermined properties of target particles of a sample medium wherein:

a) the sample medium is irradiated with light;

b) light in the form of individual photons scattered in the sample medium is detected by a detection device;

c) the time of detection of each scattered photon is determined;

d) the density of the target particles is so chosen that on average less than one target particle is present in an observed volume element of the sample medium (sample space) and e) the measured detection times are evaluated so as to determine time intervals during which target particles were individually present in the sample space;

characterised in that f) out of the times of detection measured in a time interval selected from among the time intervals, at least one time-dependent function limited to the selected time interval is formed and indicates a number of times of detection measured per predetermined unit time, the predetermined unit time being considerably shorter than the selected time interval;

g) a correlation function of the at least one function is calculated, and h) the predetermined properties of the target particles are determined by using the correlation function.

16. A method according to claim 15, characterised in that when the average value of the time intervals between the time of detection of a predetermined number of successively detected photons falls below a predetermined value, this is used as a decision criterion for the presence of an individual target particle in the sample space.

17. A method according to claim 15, characterised in that when an average value of the time intervals between the times of detection of photons successively detected in a predetermined time interval falls below a predetermined value, this is used as a decision criterion for the presence of an individual target particle in the sample space.

18. An arrangement for working the method according to claim 1 comprising:

a) at least one light source (20) which transmits modulated light having a predetermined period;

b) a sample space in which particles of a sample medium are irradiated with the light from the light source;

c) a device (18) for detecting individual photons from the sample space and constructed so that when a photon from the sample space is detected it delivers a pulse at a first output (11) and determines and defines the delay time as the time interval between the time of detection of each photon and a reference time within the associated period of the irradiating light and delivers the delay time in the form of digital data at a second output (12), and d) an evaluation device coupled to the first and second output of the detection device for receiving and evaluating the digital data;

characterised in that e) the evaluating device comprises a computer unit (27) coupled to the second output, two counters (17, 18) each having start and stop inputs, and a change-over device (24) which couples the start and stop inputs of the counters to the first output (11) of the detection device, f) wherein the change-over device switches the counters on and off in opposite directions at each pulse output by the detection device, so that one counter counts while the other counter is stopped and/or delivers the count, the cycle time of the counters being predetermined by a clock generator device (25), and g) the counts are transferable to the computer unit (27) in order to determine the properties of the target particles.

19. An arrangement according to claim 18, characterised in that the counters (17, 18) are so connected that they are reset after stopping and before restarting.

20. An arrangement according to claim 18, characterised in that the evaluating device is so constructed that on receipt of an electric pulse from the first output (11) it can store the digital data output by the detection device (8) and associate them with a count of the counters (17, 18).

21. An arrangement according to claim 18, characterised in that the counters (17, 18) are followed by at least one intermediate memory (26) for storing the count or counts before transfer to the computer unit (27).

22. An arrangement according to claim 18, characterised in that the computer unit (27) comprises a computer which has a digital input and output card (28) for receiving the digital data, and in that the data-receiving card is triggerable by the pulses (11) from the detection device (8).

23. An arrangement according to claim 18, characterised in that the detection device (8) comprises more than one detector.

24. An arrangement according to claim 18, characterised in that the detection device (8) comprises an optical arrangement in the form of a confocal microscope or a near-field microscope.

* * * * *